United States Patent [19]

Soares et al.

[11] Patent Number: 4,849,217

[45] Date of Patent: Jul. 18, 1989

[54] NOVEL ISOLATES OF BACILUS THURINGIENSIS HAVING ACTIVITY AGAINST THE ALFALFA WEEVIL, HYPERA BRUNNEIPENNIS

[75] Inventors: George G. Soares; Robert C. Everich; Jewel Payne, all of San Diego, Calif.

[73] Assignee: Mycogen Corporation, San Diego, Calif.

[21] Appl. No.: 123,023

[22] Filed: Nov. 19, 1987

[51] Int. Cl.⁴ ............................................. A01N 63/00
[52] U.S. Cl. ...................................... 424/93; 435/242; 435/832
[58] Field of Search ...................... 424/84, 93; 435/68, 435/832, 242; 514/773, 972

[56] References Cited

U.S. PATENT DOCUMENTS

| | | | |
|---|---|---|---|
| 3,946,107 | 3/1976 | Westall | 424/93 |
| 3,950,225 | 4/1976 | Skole et al. | 435/832 |
| 4,000,258 | 12/1976 | Shieh et al. | 424/93 |
| 4,797,276 | 1/1989 | Herrnstadt et al. | 435/832 |

OTHER PUBLICATIONS

Couch, T. L. (1980) "Mosquito Pathogenicity of *Bacillus thuringiensis* var. Israelensis," Developments in Industrial Microbiology 22:61-76.

Beegle, Clayton C. (1978) "Use of Entomogenous Bacteria in Agroecosystems," Developments in Industrial Microbiology 20:97-104.

Krieg, V. A., A. M. Huger, G. A. Langenbruch, W. Schnetter (1983) "*Bacillus thuringiensis* var. tenebrionis; a New Pathotype Effective Against Coleoptera larvae," Z. ang. Ent. 96:500-508. (Best copy available of translation).

*Primary Examiner*—Ferris H. Lander
*Attorney, Agent, or Firm*—Roman Saliwanchik; David R. Saliwanchik

[57] ABSTRACT

Novel *Bacillus thuringiensis* (*B.t.*) isolates are disclosed and claimed. These novel *B.t.* isolates have activity against the Egyptian alfalfa weevil, which is known to cause heavy agricultural losses.

54 Claims, No Drawings

4,849,217

NOVEL ISOLATES OF BACILUS THURINGIENSIS HAVING ACTIVITY AGAINST THE ALFALFA WEEVIL, HYPERA BRUNNEIPENNIS

DESCRIPTION

Background of the Invention

*Bacillus thuringiensis* (*B.t.*) produces an insect toxin designated as delta endotoxin. It is synthesized by the *B.t.* sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of *B.t.* covers insect species within the order Lepidoptera, many of which are major pests in agriculture and forestry. The activity spectrum also includes the insect order Diptera, which includes mosquitoes and black flies. See Couch, T. L., (1980) "Mosquito Pathogenicity of *Bacillus thuringiensis* var. *israelensis*," Developments in Industrial Microbiology 22: 61–76; Beegle, C. C., (1978) "Use of Entomogenous Bacteria in Agroecosystems," Developments in Industrial Microbiology 20: 97–104. Krieg, et al., Z. ang. Ent. (1983) 96: 500–508, describe a B.t. isolate named *Bacillus thuringiensis* var. *tenebrionis*, which is reportedly active against two beetles in the order Coleoptera. These are Colorado potato beetle, *Leptinotarsa decemlineata*, and *Agelastica alni*.

Alfalfa Weevil

The alfalfa weevil, *Hypera postica*, and the closely related Egyptian alfalfa weevil, *Hypera brunneipennis*, are the most important insect pests of alfalfa grown in the United States, with 2.9 million acres infested in 1984. An annual sum of 20 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

Chemical insecticides play a major role in effective alfalfa weevil control. However, there are several problems associated with their use including:

1. acute mammalian toxicity: several of the most effective insecticides used for weevil control are highly toxic to humans and other mammals, and are sold on a restricted basis in many states. Toxic residues are an additional problem for hay sold as feed for livestock.

2. honeybee toxicity: the honeybee is sensitive to some of the insecticides used for alfalfa weevil control. Because alfalfa is the major source of nectar for commercial honeybee colonies in the U.S., the use of insecticides with honeybee toxicity is incompatible with the needs of the honey producers.

3. toxicity to natural enemies: the insect parasites and predators which normally help control populations of minor alfalfa pests (aphids, spider mites, leafhoppers, caterpillars) are highly susceptible to all insecticides presently used for alfalfa weevil control. Reductions in the numbers of beneficial insects can result in increased populations of these once minor pests (secondary pests outbreaks), and in the consequent application of additional insecticides. Secondary pest outbreaks of aphids and mites often lead to serious yield reductions.

At present there is a need for more effective control agents, particularly efficacious agents that act selectively and do not cause the secondary outbreaks of mites and aphids that can be so devastating to alfalfa.

BRIEF SUMMARY OF THE INVENTION

Disclosed and claimed are novel isolates of *Bacillus thuringiensis* (*B.t.*) useful for the control of *Hypera brunneipennis*, the Egyptian alfalfa weevil (EAW). Some of the isolates of the subject invention have shown high activity against EAW. Furthermore, these isolates have several unique characteristics that serve to distinguish them from all previously described strains.

The *B.t.* isolates of the invention can be cultured and the toxin that is produced can be recovered by standard procedures, formulated and can be tested against larvae of EAW using several procedures.

In tests of these isolates, preparations were applied to alfalfa leaflets. Second instar EAW were placed on treated foliage and allowed to feed for 4 days. Observed mortality ranged from about 40% to about 100%.

The novel *B.t.* isolates are named *B.t.* isolate PS-52A1, *B.t.* isolate PS-98A3, *B.t.* isolate PS-74G1, *B.t.* isolate PS-62B1, *B.t.* isolate PS-17, *B.t.* isolate PS-33F2, *B.t.* isolate PS-45B1, *B.t.* isolate PS-84C3, *B.t.* isolate PS-86A1, *B.t.* isolate 80JJ1, *B.t.* isolate 80PP3, and *B.t.* isolate 80PP4.

The subject invention also includes mutants of the novel isolates which have substantially the same pesticidal properties as the parent isolates. Procedures for making mutants are well known in the microbiological art. Ultraviolet light and nitrosoguanidine are used extensively toward this end.

Further, the invention also includes the treatment of substantially intact cells of the isolates to prolong the pesticidal activity when the substantially intact cells are applied to the environment of a target pest. Such treatment can be by chemical or physical means, or a combination of chemical and physical means, so long as the technique does not deleteriously affect the properties of the pesticide, nor diminish the cellular capability in protecting the pesticide. The treated *B.t.* cell acts as a protective coating for the pesticidal toxin. The toxin becomes available to act as such upon ingestion by a target insect.

DETAILED DESCRIPTION OF THE INVENTION

The novel *B.t.* isolates of the subject invention have different inclusion bodies as shown in the following Table 1.

TABLE 1

| | B.t. PS Isolates Active Against Alfalfa Weevil | | | |
|---|---|---|---|---|
| PS # | Inclusion | Major Proteins | % Mortality Pellet | % Mortality Supernatant |
| 17 | amorph. | 140,90,60KD | 92,67 | 67 |
| 33F2 | long BP | 140,115,90, 60 | 75,100 | 43 |
| 45B1 | long slender & sm. round | 140,90,60 | 92,100 | 50 |
| 52A1 | surf board & | 70,50 | 60,100 | 75 |

TABLE 1-continued

B.t. PS Isolates Active Against Alfalfa Weevil

| PS # | Inclusion | Major Proteins | % Mortality Pellet | % Mortality Supernatant |
|---|---|---|---|---|
| 62B1 | 2 sm. inc. long slender, round | | 100,92 | |
| 74G1 | dark, spore-shaped-2/cell | 140,115,90, 60 | 89,100 | 75 |
| 84C3 | lg. amorph. | 80,70 | 33,100 | 50 |
| 86A1 | sphere, ovoid 3/cell | 50 | 50,100 | 42 |
| 98A3 | sphere | 140,115,90, 60 | 100 | 67 |
| 80JJ1 | many sm. amorph. | 135,100,50 | | |
| 80PP3 | 1 long, 1 flat attached | 45 | | |
| 80PP4 | spherical | 130 | | |

The results present in Table 1, supra, are a compilation of the characteristics and the test results for all the novel *B.t.* isolates of the invention.

The novel isolates of the subject invention have been deposited in the permanent collection of the Agricultural Research Service Patent Culture Collection (NRRL), Northern Region Research Center, 1815 North University Street, Peoria, Ill. 61604, U.S.A. The accession numbers and deposit dates are as follows:

| Isolate | Accession number | Deposit date |
|---|---|---|
| B. thuringiensis PS17 | NRRL B-18243 | July 28, 1987 |
| B. thuringiensis PS33F2 | NRRL B-18244 | July 28, 1987 |
| B. thuringiensis PS52A1 | NRRL B-18245 | July 28, 1987 |
| B. thuringiensis PS45B1 | NRRL B-18396 | August 16, 1988 |
| B. thuringiensis PS74G1 | NRRL B-18397 | August 16, 1988 |
| B. thuringiensis PS84C3 | NRRL B-18399 | August 16, 1988 |
| B. thuringiensis PS86A1 | NRRL B-18400 | August 16, 1988 |
| B. thuringiensis PS98A3 | NRRL B-18401 | August 16, 1988 |
| B. thuringiensis PS62B1 | NRRL B-18398 | August 16, 1988 |

The subject culture have been deposited under conditions that assure access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace a deposit should the depository be unable to furnish a sample when requested, due to the condition of the deposit. All restrictions on the availability to the public of the subject culture deposits will be irrevocably removed upon the granting of a patent disclosing them.

The novel B.t. isolates of the subject invention show activity against EAW larvae upon ingestion. Preliminary tests establishing this activity were conducted by treating alfalfa leaves or an artificial diet with washed parasporal inclusions (crystals or toxin) and spores.

*B. thuringiensis* strains disclosed here can be cultured using standard art media and fermentation techniques. Upon completion of the fermentation cycle the bacteria or toxins can be harvested and formulated by means well known in the art. The active ingredients can be formulated into a wettable powder, liquid concentrate, granules or other formulations by the addition of surfactants, dispersants, inert carriers and other components to facilitate handling and application for particular target pests. These formulation and application procedures are all well known in the art and are used with commercial stains of *B. thuringiensis* (HD-1) active against Lepidoptera, e.g., caterpillars.

Formulated products can be sprayed or applied onto alfalfa foliage to control the larvae and possibly the adults of EAW. Formulated products can also be applied as a seed-coating or root treatment or total plant treatment.

The *B.t.* cells, in the substantially intact form, can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17–80. More particularly, iodine can be used under mild conditiions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B. thuringiensis* isolates

A subculture of a *B.t.* isolate can be used to inoculate the following medium, a peptone, glucose, salts medium:

| | |
|---|---|
| Bacto Peptone | 7.5 g/l |
| Glucose | 1.0 g/l |
| KH$_2$PO$_4$ | 3.4 g/l |
| KH$_2$HPO$_4$ | 4.35 g/l |
| Salt Solution | 5.0 ml/l |
| CaCl$_2$ | 5.0 ml/l |

-continued

| Salts Solution (100 ml) | |
|---|---|
| MgSO$_4$—7H$_2$O | 2.46 g |
| MnSO$_4$—H$_2$O | 0.04 g |
| ZnSO$_4$—7H$_2$O | 0.28 g |
| FeSO$_4$—7H$_2$O | 0.40 g |
| CaCl$_2$ Solution (100 ml) | |
| CaCl$_2$—2H$_2$O | 3.66 g |
| pH 7.2 | |

The salts solution and CaCl$_2$ solution are filter-sterilized and added to the autoclaved broth at the time of inoculation. Flasks are incubated at 30° C. on a rotary shaker at 200 rpm for 64 hr.

The above procedure can be readily scaled up to large fermentors by procedures well known in the art.

The *B.t.* spores, crystals, or toxins, obtained in the above fermentation, can be isolated by procedures well known in the art.

The cells can be harvested in the substantially intact form by monitoring the fermentation and recovering the cells before lysis occurs. This recovery process can be by standard procedures, as described above.

EXAMPLE 2

Activity of *Bacillus thuringiensis* isolates against *Hypera brunneipennis*, the Egyptian alfalfa weevil Each isolate was cultured as described in Example 1 in liquid shake culture. Cultures were harvested and centrifuged at 8000 rpm for 12 minutes. The supernatant was discarded and the pellet containing the spores and parasporal inclusions was resuspended in sterile water at one-tenth the original culture volume. The suspension was vortexed and ten microliters was applied to each of 5 alfalfa leaflets held on 2% agar in individual wells in a plastic tray. The suspension was allowed to dry and one second instar EAW was placed on each leaflet. Trays were then sealed and incubated for 7 days at 25° C. On day 7 mortality was determined. Observed mortality was 80–100%.

In a second series of experiments, serial dilutions of spore/crystal suspensions were applied to the surface of an artificial diet. The diet was poured into wells in a plastic tray and allowed to set before inoculation. For these experiments, each of 12 wells were inoculated by depositing 75 microliters of each test suspension onto each well, swirling the tray to ensure even distribution. Five dilutions of each spore/crystal suspension were tested. Results of these experiments are shown in Table 2. Protein concentration was quantified by scanning SDS page electrophoresis gels of alkali-solubilized test samples.

In subsequent tests, whole cultures were centrifuged and the supernatant was collected and filter sterilized. The pellet was washed and resuspended in one-half the original volume of sterile water. Both the supernatant and resuspended pellet were then assayed as described above. Results are shown in Table 3. From these tests it was evident that activity was also present in the supernatant and suggested that at least part of the activity might be due to a toxin that is excreted into the medium.

TABLE 2

Results of a dose-response experiment using two *Bacillus thuringiensis* isolates against second instar larvae of the Egyptian alfalfa weevil (EAW), *Hypera brunneipennis*; isolate 52A1, an EAW-active survey isolate, and isolate MT-38 (NRRL B-18251).

| ISOLATE NO. | DILUTION | PROTEIN CONC. µG/WELL | % MOR-TALITY | APPROX. LC$_{50}$ |
|---|---|---|---|---|
| 52A1 | 1 | 240 | 91 | 37 µg/well |
| | 2 | 120 | 92 | |
| | 3 | 60 | 67 | |
| | 4 | 30 | 58 | |
| | 5 | 15 | 17 | |
| MT-38 | 1 | 740 | 8 | |
| | 2 | 370 | 0 | |
| | 3 | 185 | 0 | |
| | 4 | 93 | 0 | |
| | 5 | 47 | 8 | |
| Controls | | 0 | 4 | |

TABLE 3

Results of Bioassays of Resuspended Pellets and Supernatants Against Alfalfa Weevil Larvae

| | % MORTALITY | |
|---|---|---|
| Isolate | Pellet | Supernatant |
| 74G1 | 89 | 75 |
| 62B1 | 100 | 67 |
| 98A3 | 100 | 67 |

We claim:

1. A process for controlling insect infestation of alfalfa, said infestation by an alfalfa weevil, which comprises contacting said infesting insect, or treating the environment of said infesting insect, with an insect-controlling effective amount of a composition comprising a *Bacillus thuringiensis* isolate selected from the group consisting of *B.t.* isolate PS-52A1, *B.t.* isolate PS-98A3, *B.t.* isolate PS-74G1, *B.t.* isolate PS-62B1, *B.t.* isolate PS-17, *B.t.* isolate PS-33F2, *B.t.* isolate PS-45B1, *B.t.* isolate PS-84C3, *B.t. isolate PS*-86A1, *B.t.* isolate 80JJ1, *B.t.* isolate 80PP3, and *B.t.* isolate 80PP4, or mutants thereof, and toxins, crystals or spores thereof.

2. The process, according to claim 1, wherein said alfalfa weevil is the Egyptian alfalfa weevil (EAW).

3. The process, according to claim 1, wherein said *Bacillus thuringiensis* isolate is *B.t.* isolate PS-52A1, or mutants thereof, and toxins, crystals and spores thereof.

4. The process, according to claim 1, wherein said *Bacillus thuringiensis* isolate is *B.t.* isolate PS-98A3, or mutants thereof, and toxins, crystals and spores thereof.

5. The process, according to claim 1, wherein said *Bacillus thuringiensis* isolate is *B.t.* isolate PS-62B1, or mutants thereof, and toxins, crystals and spores thereof.

6. The process, according to claim 1, wherein said *Bacillus thuringiensis* isolate is *B.t.* isolate PS-74G1, or mutants thereof, and toxins, crystals and spores thereof.

7. The process, according to claim 1, wherein said *Bacillus thuringiensis* isolate is *B.t.* isolate PS-17, or mutants thereof, and toxins, crystals and spores thereof.

8. The process, according to claim 1, wherein said *Bacillus thuringiensis* isolate is *B.t.* isolate PS-33F2, or mutants thereof, and toxins, crystals and spores thereof.

9. The process, according to claim 1, wherein said *Bacillus thuringiensis* isolate is *B.t.* isolate PS-45B1, or mutants thereof, and toxins, crystals and spores thereof.

10. The process, according to claim 1, wherein said *Bacillus thuringiensis* isolate is *B.t.* isolate PS-84C3, or mutants thereof, and toxins, crystals and spores thereof.

11. The process, according to claim 1, wherein said *Bacillus thuringiensis* isolate is *B.t.* isolate PS-86A1, or mutants thereof, and toxins, crystals and spores thereof.

12. The process, according to claim 1, wherein said *Bacillus thuringiensis* isolate is *B.t.* isolate 80JJ1, or mutants thereof, and toxins, crystals and spores thereof.

13. The process, according to claim 1, wherein said *Bacillus thuringiensis* isolate is *B.t.* isolate 80PP3, or mutants thereof, and toxins, crystals and spores thereof.

14. The process, according to claim 1, wherein said *Bacillus thuringiensis* isolate is *B.t.* isolate 80PP4, or mutants thereof, and toxins, crystals and spores thereof.

15. A novel *Bacillus thuringiensis* isolate selected from the group consisting of *B.t.* isolate PS-52A1, *B.t.* isolate PS-98A3, *B.t.* isolate PS-74G1, *B.t.* isolate PS-62B1, *B.t.* isolate PS-17, *B.t.* isolate PS-33F2, *B.t.* isolate PS-45B1, *B.t.* isolate PS-84C3, *B.t.* isolate PS-86A1, *B.t.* isolate 80JJ1, *B.t.* isolate 80PP3, and *B.t.* isolate 80PP4, or mutants thereof.

16. A novel *Bacillus thuringiensis* isolate, according to claim 15, named *B.t.* isolate PS-52A1, or mutants thereof.

17. A novel *Bacillus thuringiensis* isolate, according to claim 15, named *B.t.* isolate PS-98A3, or mutants thereof.

18. A novel *Bacillus thuringiensis* isolate, according to claim 15, named *B.t.* isolate PS-74G1, or mutants thereof.

19. A novel *Bacillus thuringiensis* isolate, according to claim 15, named *B.t.* isolate PS-62B1, or mutants thereof.

20. A novel *Bacillus thuringiensis* isolate, according to claim 15, named *B.t.* isolate PS-17, or mutants thereof.

21. A novel *Bacillus thuringiensis* isolate, according to claim 15, named *B.t.* isolate PS-33F2, or mutants thereof.

22. A novel *Bacillus thuringiensis* isolate, according to claim 15, named *B.t.* isolate PS-45B1, or mutants thereof.

23. A novel *Bacillus thuringiensis* isolate, according to claim 15, named *B.t.* isolate PS-84C3, or mutants thereof.

24. A novel *Bacillus thuringiensis* isolate, according to claim 15, named *B.t.* isolate PS-86A1, or mutants thereof.

25. A novel *Bacillus thuringiensis* isolate, according to claim 15, named *B.t.* isolate 80JJ1, or mutants thereof.

26. A novel *Bacillus thuringiensis* isolate, according to claim 15, named *B.t.* isolate 80PP3, or mutants thereof.

27. A novel *Bacillus thuringiensis* isolate, according to claim 15, named *B.t.* isolate 80PP4, or mutants thereof.

28. A process, according to claim 1, wherein substantially intact *B.t.* cells of the isolates listed, or mutants thereof, are treated to prolong the pesticidal activity when the substantially intact *B.t.* cells are applied to the environment of said alfalfa weevil.

29. A composition of matter comprising a *Bacillus thuringiensis* isolate selected from the group consisting of *B.t.* isolate PS-52A1, *B.t.* isolate PS-98A3, *B.t.* isolate PS-74G1, *B.t.* isolate PS-62B1, *B.t.* isolate PS-17, *B.t.* isolate PS-33F2, *B.t.* isolate PS-45B1, *B.t. isolate PS-84C3*, *B.t.* isolate PS-86A1, *B.t.* isolate 80JJ1, *B.t.* isolate 80PP3, and *B.t.* isolate 80PP4 or mutants thereof, and toxins, crystals or spores thereof.

30. The composition of matter, according to claim 29, wherein said *Bacillus thuringiensis* is *B.t.* isolate PS-52A1, or mutants thereof, and toxins, crystals or spores thereof.

31. The composition of matter, according to claim 29, wherein said *Baccillus thuringiensis* is *B.t.* isolate PS-98A3, or mutants thereof, and toxins, crystals or spores thereof.

32. The composition of matter, according to claim 29, wherein said *Bacillus thuringiensis* is *B.t.* isolate PS-74G1, or mutants thereof, and toxins, crystals or spores thereof.

33. The composition of matter, according to claim 29, wherein said *Bacillus thuringiensis* is *B.t.* isolate PS-62B1, or mutants thereof, and toxins, crystals or spores thereof.

34. The composition of matter, according to claim 29, wherein said *Bacillus thuringiensis* is *B.t.* isolate PS-17, or mutants thereof, and toxins, crystals or spores thereof.

35. The composition of matter, according to claim 29, wherein said *Bacillus thuringiensis* is *B.t.* isolate PS-33F2, or mutants thereof, and toxins, crystals or spores thereof.

36. The composition of matter, according to claim 29, wherein said *Bacillus thuringiensis* is *B.t.* isolate PS-45B1, or mutants thereof, and toxins, crystals or spores thereof.

37. The composition of matter, according to claim 29, wherein said *Bacillus thuringiensis* is *B.t.* isolate PS-84C3, or mutants thereof, and toxins, crystals or spores thereof.

38. The composition of matter, according to claim 29, wherein said *Bacillus thuringiensis* is *B.t.* isolate PS-86A1, or mutants thereof, and toxins, crystals or spores thereof.

39. The composition of matter, according to claim 29, wherein said *Bacillus thuringiensis* is *B.t.* isolate 80JJ1, or mutants thereof, and toxins, crystals or spores thereof.

40. The composition of matter, according to claim 29, wherein said *Bacillus thuringiensis* is *B.t.* isolate 80PP3 or mutants thereof, and toxins, crystals or spores thereof.

41. The composition of matter, according to claim 29, wherein said *Bacillus thuringiensis* is *B.t.* isolate 80PP4, or mutants thereof, and toxins, crystals or spores thereof.

42. A toxin active against the Egyptian alfalfa weevil producible by a *Bacillus thuringiensis* isolate selected from the group consisting of *B.t.* isolate PS-52A1, *B.t.* isolate PS-98A3, *B.t.* isolate PS-74G1, *B.t.* isolate PS-62B1, *B.t.* isolate PS-17, *B.t.* isolate PS-33F2, *B.t.* isolate PS-45B1, *B.t.* isolate PS-84C3, *B.t.* isolate PS-86A1, *B.t.* isolate 80JJ1, *B.t.* isolate 80PP3, and *B.t.* isolate 80PP4, or mutants thereof.

43. A toxin, according to claim 42, producible by *B.t.* isolate PS-52A1, or mutants thereof.

44. A toxin, according to claim 42, producible by *B.t.* isolate PS-98A3, or mutants thereof.

45. A toxin, according to claim 42, producible by *B.t.* isolate PS-74G1, or mutants thereof.

46. A toxin, according to claim 42, producible by *B.t.* isolate PS-62B1, or mutants thereof.

47. A toxin, according to claim 42, producible by *B.t.* isolate PS-17, or mutants thereof.

48. A toxin, according to claim 42, producible by *B.t.* isolate PS-33F2, or mutants thereof.

49. A toxin, according to claim 42, producible by *B.t.* isolate PS-45B1, or mutants thereof.

50. A toxin, according to claim 42, producible by *B.t.* isolate PS-84C3, or mutants thereof.

51. A toxin, according to claim 42, producible by *B.t.* isolate PS-86A1, or mutants thereof.

52. A toxin, according to claim 42, producible by *B.t.* isolate 80JJ1, or mutants thereof.

53. A toxin, according to claim 42, producible by *B.t.* isolate 80PP3, or mutants thereof.

54. A toxin, according to claim 42, producible by *B.t.* isolate 80PP4, or mutants thereof.

* * * * *

UNITED STATES PATENT AND TRADEMARK OFFICE
CERTIFICATE OF CORRECTION

PATENT NO. : 4,849,217

DATED : July 18, 1989

INVENTOR(S) : George G. Soares, Robert C. Everich, Jewel Payne

It is certified that error appears in the above-identified patent and that said Letters Patent is hereby corrected as shown below:

On the title page, item [54] and
Column 1:   line 1: Novel Isolates of "Bacilus" should read ---Novel Isolates of Bacillus--
Column 3:   line 41: The subject "culture" should read --The subject cultures--

Signed and Sealed this

Twenty-seventh Day of November, 1990

Attest:

HARRY F. MANBECK, JR.

*Attesting Officer*  *Commissioner of Patents and Trademarks*